US00PP16013P2

(12) United States Plant Patent
van Geest

(10) Patent No.: US PP16,013 P2
(45) Date of Patent: Sep. 27, 2005

(54) *FICUS* PLANT NAMED 'BLACK DIAMOND'

(50) Latin Name: *Ficus benjamina*
Varietal Denomination: Black Diamond

(75) Inventor: Jan van Geest, s'Gravenzande (NL)

(73) Assignee: Plantenkwekerij J. Van Geest, B.V., S'Gravenzande (NL)

( * ) Notice: Subject to any disclaimer, the term of this patent is extended or adjusted under 35 U.S.C. 154(b) by 21 days.

(21) Appl. No.: 10/806,389

(22) Filed: Mar. 23, 2004

(51) Int. Cl.[7] ..... A01H 5/00
(52) U.S. Cl. ..... Plt./211
(58) Field of Search ..... Plt./211

*Primary Examiner*—Anne Marie Grunberg
*Assistant Examiner*—Annette H Para
(74) *Attorney, Agent, or Firm*—Foley & Lardner, LLP

(57) ABSTRACT

A new and distinct variety of *Ficus benjamina* designated 'Black Diamond', particularly characterized by variegated leaves with very dark green foliage with amorphous, irregularly shaped and irregularly patterned spots of yellow green along the midrib of the leaf. 'Black Diamond' is heavily branching with an upright growth habit.

2 Drawing Sheets

Latin name of the genus and species of the plant claimed: *Ficus benjamina*.
Variety denomination: Black Diamond.

BACKGROUND OF THE INVENTION

The present invention relates to a new and distinct cultivar of *Ficus benjamina*. The varietal denomination of the new cultivar is 'Black Diamond'. The new variety was discovered as a mutation in a controlled planting of *Ficus benjamina* 'Midnight' in a greenhouse in s'Gravenzande, The Netherlands in June, 2001.

SUMMARY OF THE INVENTION

The new variety is a mutation of the *Ficus* variety 'Midnight' (U.S. Plant Pat. No. 9,856 ), and was selected by the inventor, Jan van Geest. The mutation was selected among plants of 'Midnight' which were grown in a controlled environment in a glasshouse in s'Gravenzande, The Netherlands in June, 2001. The new variety was first asexually propagated by vegetative cutting in August 2001, in s'Gravenzande, The Netherlands. Asexual reproduction through succeeding generations has established that the combination of characteristics as herein disclosed for the new cultivar are firmly fixed and retained throught successive generations of asexual reproduction.

In comparison to the parent plant, 'Midnight', the leaf color of 'Black Diamond' is variegated. The leaves of 'Black Diamond' are very dark green (near 137 A, new foliage, upper side), with an amorphous, irregularly shaped and irregularly patterned spot of yellow-green (RHS 144A) located along the midrib of the leaf. The leaves of 'Midnight' by comparison are 137B (new foliage, upper side). In addition, 'Black Diamond' varies from the parent plant in leaf and petiole size. The leaves of 'Black Diamond' are narrower, 3.5 cm, as compared to 4 cm leaf width of 'Midnight', and shorter, 9 cm, as compared to 11 cm long leaves of 'Midnight'. The petioles of 'Black Diamond' are shorter, approximately 5 mm in length, as compared to 18 mm long petioles of 'Midnight'.

Of the commercial cultivars known to the Inventor, the most similar in comparison to the new *Ficus* cultivar 'Black Diamond' is the *Ficus* cultivar 'Indigo' (U.S. Plant Pat. No. 9,491). The *Ficus* cultivar 'Indigo' was discovered and selected by the Inventor, and is the parental cultivar of 'Midnight' which is the parental cultivar of 'Black Diamond'. Side-by-side comparisons between 'Black Diamond' and 'Indigo' were conducted by the Inventor, and the two *Ficus* cultivars differ primarily with respect to the variegated spot pattern along the mid-rib of the plant foliage. First, the variegated spot pattern along the mid-rib of the foliage in 'Black Diamond' is more pronounced than in 'Indigo'. Second, the R.H.S. color designation of the variegated spot in 'Indigo' is green (RHS 137C to 137D), whereas the R.H.S. color designation of the variegated spot in 'Black Diamond' is yellow-green (RHS 144A). Third, the yellow-green variegated spot color of 'Black Diamond' is more pronounced in contrast to the dark green color (RHS 137A) of the foliage surface. Fourth, the growth and branching habit of the 'Black Diamond' is regular and upright, whereas the growth and branching habit of 'Indigo' is extremely vigorous with somewhat irregular branching.

BRIEF DESCRIPTION OF THE INVENTION

The following traits have been repeatedly observed and are determined to be basic characteristics of 'Black Diamond' which in combination distinguish this *Ficus* as a new and distinct cultivar from parent cultivar 'Midnight' and other *Ficus* cultivars:

1. Variegated colored leaves, having a dark green colored leaf with a yellow-green spot;
2. Irregularly shaped leaves; and
3. Irregular patterned spots of yellow-green located along the midrib of the leaf
4. Heavily branching, upright growth habit.

BRIEF DESCRIPTION OF THE DRAWINGS

The accompanying photographic drawings show a specimen of the new cultivar as true to color as is reasonably possible.

The first photographic drawing is a side view of 'Black Diamond' in its entirety showing the growth habit.

The second photographic drawing is a close up of the foliage of 'Black Diamond'. Phenotypic expression may vary depending on light, environmental and cultural conditions.

DETAILED DESCRIPTION OF THE NEW VARIETY

'Black Diamond' has not been observed under all possible environmental conditions. The phenotypic expression may vary with variations in environment such as temperature, light intensity, day length and cultural conditions, without a change in the genotype of the plant.

The following observations and descriptions are of a plant grown in a shade house covered with plastic wrap providing 73% shade in Homestead, Fla., during the months of January through July, 2003. Color references are to The Royal Horticultural Society Colour Chart (R.H.S.). The color references are as approximate as possible as color depends to a degree on horticultural practices such as light level and fertilization rates.

PLANT

Form: Medium compact, somewhat weeping, upwardly branching, ascending regularly and richly branching.

Growth: Lateral branches are approximately at a 30 to 45 degree angle to the trunk, but slightly weeping at the top; maximum height 1 meter.

Growth habit: Heavily branching, upright.

Foliage:

*Size.*—About 3.5 cm wide by 9 cm long (to leaf tip).

*Color.*—New foliage: Upper side green near 137 A, with the spot along the midrib of leaf being closest to yellow-green 144A; underside 138A with the spot along the midrib closest to 139C. Old foliage: Upper side green 131 with the spot along the midrib near yellow-green 144A; underside near 137C with the spot along the midrib near 138D.

*Shape.*—Ovate with acuminate leaf tip slightly coarsely sinuate and glabrous.

*Texture.*—Smooth, leathery, glossy, underside smooth, matte.

*Veination.*—Single mid-rib vein running from petiole to leaf tip, convex on underside, light green near 145B.

*Margin.*—Entire, slightly undulate.

*Serration.*—None.

*Stipules.*—Leaves are glabrous.

*Petiole.*—Closest to 144A; about 5 mm long.

*Disease resistance.*—No particular claim observation made.

*Rachis.*—None.

Wood:

*New shoots.*—Color near 144A; smooth.

*Old wood.*—Color near 197B; no flowers or fruit observed to date.

*Internode spacing.*—About 30 mm.

*Preferred growing conditions.*—20 degrees C. to 32 degrees C.

*Reproductive organs.*—None observed.

*Temperature range.*—To 2 degrees C.

I claim:

1. A new and distinct variety of *Ficus benjamina* designated 'Black Diamond', as illustrated and described herein.

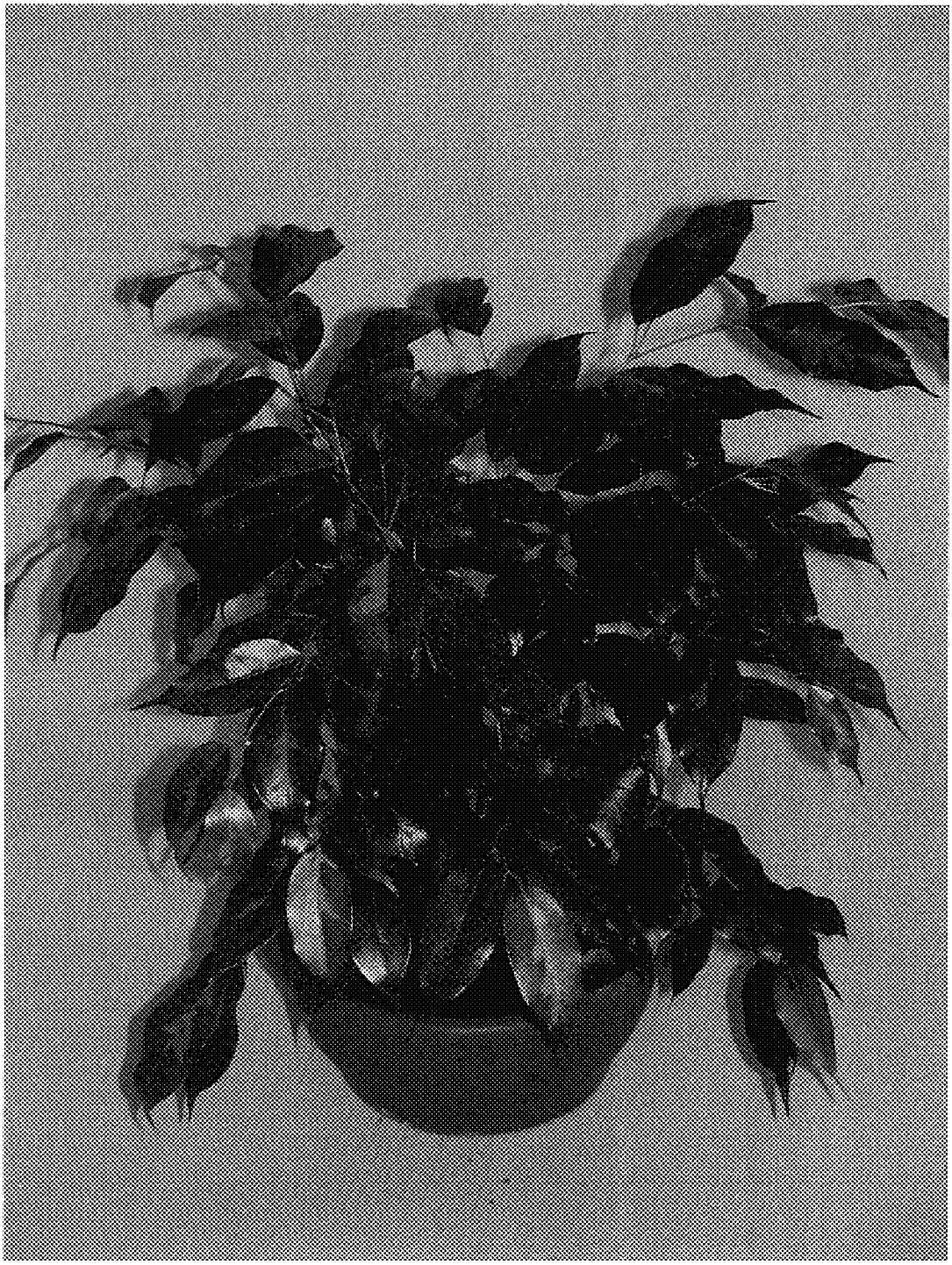

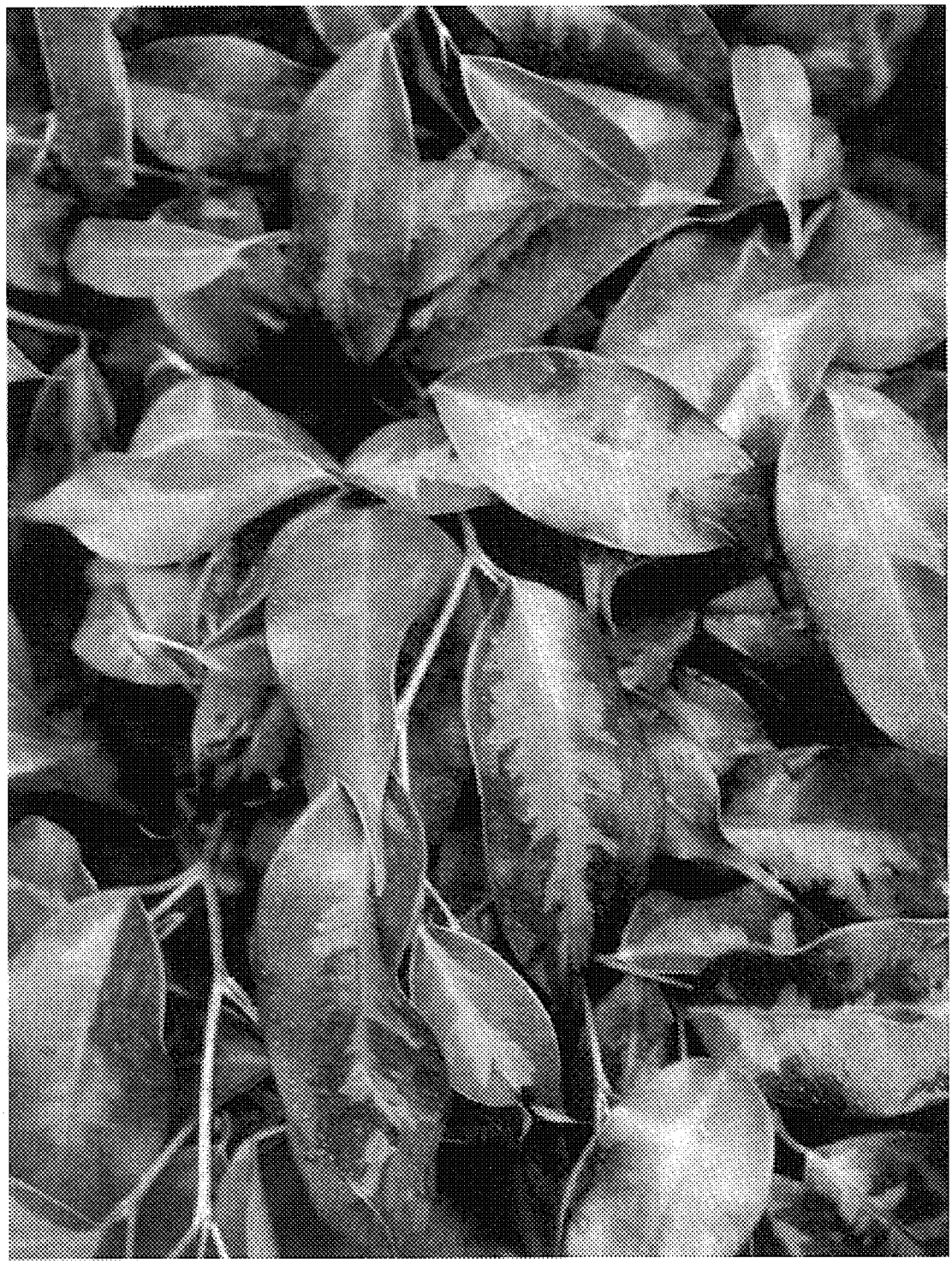

* * * * *